United States Patent
Bajic (10) Patent No.: US 9,082,603 B2
(45) Date of Patent: Jul. 14, 2015

(54) ATMOSPHERIC PRESSURE ION SOURCE BY INTERACTING HIGH VELOCITY SPRAY WITH A TARGET

(71) Applicant: Micromass UK Limited, Wilmslow (GB)

(72) Inventor: Stevan Bajic, Sale (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/563,149

(22) Filed: Dec. 8, 2014

(65) Prior Publication Data

US 2015/0155151 A1  Jun. 4, 2015

Related U.S. Application Data

(63) Continuation of application No. 14/451,513, filed on Aug. 5, 2014, now Pat. No. 8,921,777, which is a continuation of application No. 14/113,151, filed as application No. PCT/GB2012/050888 on Apr. 20, 2012, now Pat. No. 8,809,777.

(60) Provisional application No. 61/614,734, filed on Mar. 23, 2012, provisional application No. 61/478,725, filed on Apr. 25, 2011.

(30) Foreign Application Priority Data

Apr. 20, 2011 (GB) .................................. 1106694.1
Mar. 21, 2012 (GB) .................................. 1204937.5

(51) Int. Cl.
*H01J 49/10* (2006.01)
*H01J 49/26* (2006.01)
*H01J 49/24* (2006.01)

(52) U.S. Cl.
CPC ................. *H01J 49/10* (2013.01); *H01J 49/24* (2013.01); *H01J 49/26* (2013.01)

(58) Field of Classification Search
USPC ....................................... 250/288, 423 R, 424
See application file for complete search history.

(56) References Cited

U.S. PATENT DOCUMENTS

| | | | | |
|---|---|---|---|---|
| 5,986,259 | A * | 11/1999 | Hirabayashi et al. | ......... 250/288 |
| 6,294,779 | B1 | 9/2001 | Apffel et al. | |
| 6,462,336 | B1 | 10/2002 | Bajic | |
| 7,034,291 | B1 | 4/2006 | Fischer et al. | |
| 7,189,977 | B2 | 3/2007 | Yamaguchi et al. | |
| 7,368,728 | B2 | 5/2008 | Cristoni et al. | |

(Continued)

FOREIGN PATENT DOCUMENTS

| | | |
|---|---|---|
| JP | 59153164 | 9/1984 |
| JP | 10267806 | 10/1998 |

(Continued)

OTHER PUBLICATIONS

Browner et al., "*Aerosol Transport Model for Atomic Spectrometry*", Analytical Chemistry, vol. 54, No. 8, pp. 1411-1419, 1982.

*Primary Examiner* — Kiet T Nguyen
(74) *Attorney, Agent, or Firm* — Diederiks & Whitelaw, PLC (57) ABSTRACT

An ion source is disclosed comprising a nebulizer and a target. The nebulizer is arranged and adapted to emit, in use, a stream of analyte droplets which are caused to impact upon the target and to ionize analyte to form a plurality of analyte ions.

29 Claims, 7 Drawing Sheets

(56) References Cited

U.S. PATENT DOCUMENTS

| | | |
|---|---|---|
| 7,411,186 B2 | 8/2008 | Mordehai |
| 7,960,711 B1 | 6/2011 | Sheehan et al. |
| 7,982,185 B2 | 7/2011 | Whitehouse et al. |
| 8,097,845 B2 | 1/2012 | Roach et al. |
| 8,232,520 B2 | 7/2012 | Cristoni |
| 8,513,599 B2 | 8/2013 | Franzen et al. |
| 2011/0031392 A1* | 2/2011 | McEwen et al. ............ 250/283 |

FOREIGN PATENT DOCUMENTS

| | | |
|---|---|---|
| JP | 1151902 | 2/1999 |
| JP | 2002190272 | 7/2002 |

* cited by examiner

Prior Art

ATMOSPHERIC PRESSURE ION SOURCE BY INTERACTING HIGH VELOCITY SPRAY WITH A TARGET

CROSS-REFERENCE TO RELATED APPLICATION

This application is a continuation of U.S. patent application Ser. No. 14/451,513 filed Aug. 5, 2014 which is a continuation of U.S. patent application Ser. No. 14/113,151 filed Oct. 21, 2013, which is the National Stage of International Application No. PCT/GB2012/050888, filed 20 Apr. 2012, which claims priority from and the benefit of U.S. Provisional Patent Application Ser. No. 61/614,734 filed Mar. 23, 2012, United Kingdom Patent Application No. 1204937.5 filed on Mar. 21, 2012, U.S. Provisional Patent Application Ser. No. 61/478,725 filed on 25 Apr. 2011 and United Kingdom Patent Application No. 1106694.1 filed on 20 Apr. 2011. The entire contents of these applications are incorporated herein by reference.

BACKGROUND OF THE PRESENT INVENTION

The present invention relates to an ion source for a mass spectrometer and a method of ionising a sample. The preferred embodiment relates to a mass spectrometer and a method of mass spectrometry.

Atmospheric Pressure Ionization ("API") ion sources are commonly used to ionize the liquid flow from HPLC or UPLC chromatography devices prior to analyzing the resulting gas phase ions via a mass spectrometer. Two techniques which are most commonly used comprise Electrospray Ionization ("ESI") and Atmospheric Pressure Chemical Ionization ("APCI"). ESI is optimal for moderate to high polarity analytes and APCI is optimal for non-polar analytes. API ion sources that combine both of these techniques have been proposed and realized in designs that simultaneously combine ESI and APCI ionization using geometries that ensure that the electric fields generated by each technique are shielded and are independent of one another. These so called "multimode" ion sources have the advantage of being able to ionize analyte mixtures containing a wide range of polarities in a single chromatographic run without the need to switch between different ionization techniques. U.S. Pat. No. 7,034,291 discloses a ESI/APCI multimode ionization source comprising an ESI ion source and a downstream corona needle and U.S. Pat. No. 7,411,186 discloses a multimode ESI/APCI ion source. The known multimode ion sources suffer from the problem of being mechanically complex.

Other universal or multimode ionization sources have been proposed for interfacing liquid chromatography to mass spectrometry. One such example is a Surface Activated Chemical Ionization ("SACI") ion source which directs a vapour stream from a heated nebuliser probe towards a broad area charged target plate which is situated close to the ion inlet aperture of the mass spectrometer and 15-20 mm away from the end of the nebuliser. The spray point of the SACI ion source is within the heated nebuliser probe so that the typical distance between the spray point of the SACI ion source and the target plate is 70 mm. This geometry with a relatively large distance between the sprayer and the target produces a divergent spray with a dispersed reflected flow at the target which generally results in lower sensitivities when compared to optimized ESI and APCI sources. U.S. Pat. No. 7,368,728 discloses a known Surface Activated Chemical Ionisation ion source.

It is also known to place a small target in the form of a bead at close proximity to the nebulised spray point in impactor nebulisers which are used in atomic absorption spectroscopy. An impactor nebuliser is, for example, disclosed in Anal. Chem. 1982, 54, 1411-1419. The known impactor nebuliser is not used to ionise a sample.

It is desired to provide an improved ion source for a mass spectrometer.

SUMMARY OF THE INVENTION

According to an aspect of the present invention there is provided an ion source comprising:

one or more nebulisers and one or more targets;

wherein one or more nebulisers are arranged and adapted to emit, in use, a stream predominantly of droplets which are caused to impact upon the one or more targets and to ionise the droplets to form a plurality of ions.

The droplets preferably comprise analyte droplets and the plurality of ions preferably comprise analyte ions.

However, according to another embodiment the droplets may comprise reagent droplets and the plurality of ions may comprise reagent ions.

According to the preferred embodiment reagent ions which are created may react, interact with or transfer charge to neutral analyte molecules and cause the analyte molecules to become ionised. Reagent ions may also be used to enhance the formation of analyte ions.

According to an embodiment one or more tubes may be arranged and adapted to supply one or more analyte or other gases to a region adjacent the one or more targets.

The reagent ions are preferably arranged so as to ionise the analyte gas to form a plurality of analyte ions.

An analyte liquid may be supplied to the one or more targets and may be ionised to form a plurality of analyte ions and/or a reagent liquid may be supplied to the one or more targets and may be ionised to form reagent ions which transfer charge to neutral analyte atoms or molecules to form analyte ions and/or which enhance the formation of analyte ions.

The one or more targets preferably comprise one or more apertures and wherein the analyte liquid and/or reagent liquid is supplied directly to the one or more targets and emerges from the one or more apertures.

According to an embodiment the one or more targets may be coated with one or more liquid, solid or gelatinous analytes and wherein the one or more analytes are ionised to form a plurality of analyte ions.

The one or more targets may be formed from one or more analytes and the one or more analytes may be ionised to form a plurality of analyte ions.

According to the preferred embodiment the ion source comprises an Atmospheric Pressure Ionisation ("API") ion source.

The one or more nebulisers are preferably arranged and adapted such that the majority of the mass or matter emitted by the one or more nebulisers is in the form of droplets not vapour.

Preferably, at least 50%, 55%, 60%, 65%, 70%, 75%, 80%, 85%, 90% or 95% of the mass or matter emitted by the one or more nebulisers is in the form of droplets.

The one or more nebulisers are preferably arranged and adapted to emit a stream of droplets wherein the Sauter mean diameter ("SMD", d32) of the droplets is in a range: (i) <5 µm; (ii) 5-10 µm; (iii) 10-15 µm; (iv) 15-20 µm; (v) 20-25 µm; or (vi) >25 µm.

The stream of droplets emitted from the one or more nebulisers preferably forms a stream of secondary droplets after impacting the one or more targets.

The stream of droplets and/or the stream of secondary droplets preferably traverse a flow region with a Reynolds number (Re) in the range: (i) <2000; (ii) 2000-2500; (iii) 2500-3000; (iv) 3000-3500; (v) 3500-4000; or (vi) >4000.

According to the preferred embodiment substantially at the point of the droplets impacting the one or more targets the droplets have a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

According to the preferred embodiment substantially at the point of the droplets impacting the one or more targets the droplets have a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

The mean axial impact velocity of the droplets upon the one or more targets is preferably selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The one or more targets are preferably arranged <20 mm, <19 mm, <18 mm, <17 mm, <16 mm, <15 mm, <14 mm, <13 mm, <12 mm, <11 mm, <10 mm, <9 mm, <8 mm, <7 mm, <6 mm, <5 mm, <4 mm, <3 mm or <2 mm from the exit of the one or more nebulisers.

The one or more nebulisers are preferably arranged and adapted to nebulise one or more eluents emitted by one or more devices over a period of time.

The one or more devices preferably comprise one or more liquid chromatography separation devices.

The one or more nebulisers are preferably arranged and adapted to nebulise one or more eluents, wherein the one or more eluents have a liquid flow rate selected from the group consisting of: (i) <1 μL/min; (ii) 1-10 μL/min; (iii) 10-50 μL/min; (iv) 50-100 μL/min; (v) 100-200 μL/min; (vi) 200-300 μL/min; (vii) 300-400 μL/min; (viii) 400-500 μL/min; (ix) 500-600 μL/min; (x) 600-700 μL/min; (xi) 700-800 μL/min; (xii) 800-900 μL/min; (xiii) 900-1000 μL/min; (xiv) 1000-1500 μL/min; (xv) 1500-2000 μL/min; (xvi) 2000-2500 μL/min; and (xvii) >2500 μL/min.

The one or more nebulisers may according to a less preferred embodiment comprise one or more rotating disc nebulisers.

The one or more nebulisers preferably comprise a first capillary tube having an exit which emits, in use, the stream of droplets.

The first capillary tube is preferably maintained, in use, at a potential: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV.

The first capillary tube is preferably maintained, in use, at a potential of: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200V; (xiii) −200 to −100V; (xiv) −100 to −90V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV; relative to the potential of an enclosure surrounding the ion source and/or an ion inlet device which leads to a first vacuum stage of a mass spectrometer and/or the one or more targets.

According to an embodiment a wire may be located within the volume enclosed by the first capillary tube wherein the wire is arranged and adapted to focus the stream of droplets.

According to the preferred embodiment:

(i) the first capillary tube is surrounded by a second capillary tube which is arranged and adapted to provide a stream of gas to the exit of the first capillary tube; or (ii) a second capillary tube is arranged and adapted to provide a cross flow stream of gas to the exit of the first capillary tube.

The second capillary tube preferably surrounds the first capillary tube and/or is either concentric or non-concentric with the first capillary tube.

The ends of the first and second capillary tubes are preferably either: (i) flush or parallel with each other; or (ii) protruded, recessed or non-parallel relative to each other. The exit of the first capillary tube preferably has a diameter D and the spray of droplets is preferably arranged to impact on an impact zone of the one or more targets.

The impact zone preferably has a maximum dimension of x and wherein the ratio x/D is in the range <2, 2-5, 5-10, 10-15, 15-20, 20-25, 25-30, 30-35, 35-40 or >40.

The impact zone preferably has an area selected from the group consisting of: (i) <0.01 $mm^2$; (ii) 0.01-0.10 $mm^2$; (iii) 0.10-0.20 $mm^2$; (iv) 0.20-0.30 $mm^2$; (v) 0.30-0.40 $mm^2$; (vi) 0.40-0.50 $mm^2$; (vii) 0.50-0.60 $mm^2$; (viii) 0.60-0.70 $mm^2$; (ix) 0.70-0.80 $mm^2$; (x) 0.80-0.90 $mm^2$; (xi) 0.90-1.00 $mm^2$; (xii) 1.00-1.10 $mm^2$; (xiii) 1.10-1.20 $mm^2$; (xiv) 1.20-1.30 $mm^2$; (xv) 1.30-1.40 $mm^2$; (xvi) 1.40-1.50 $mm^2$; (xvii) 1.50-1.60 $mm^2$; (xviii) 1.60-1.70 $mm^2$; (xix) 1.70-1.80 $mm^2$; (xx) 1.80-1.90 $mm^2$; (xxi) 1.90-2.00 $mm^2$; (xxii) 2.00-2.10 $mm^2$; (xxiii) 2.10-2.20 $mm^2$; (xxiv) 2.20-2.30 $mm^2$; (xxv) 2.30-2.40 $mm^2$; (xxvi) 2.40-2.50 $mm^2$; (xxvii) 2.50-2.60 $mm^2$; (xxviii) 2.60-2.70 $mm^2$; (xxix) 2.70-2.80 $mm^2$; (xxx) 2.80-2.90 $mm^2$; (xxxi) 2.90-3.00 $mm^2$; (xxxii) 3.00-3.10 $mm^2$; (xxxiii) 3.10-3.20 $mm^2$; (xxxiv) 3.20-3.30 $mm^2$; (xxxv) 3.30-3.40 $mm^2$; (xxxvi) 3.40-3.50 $mm^2$; (xxxvii) 3.50-3.60 $mm^2$; (xxxviii) 3.60-3.70 $mm^2$; (xxxix) 3.70-3.80 $mm^2$; (xl) 3.80-3.90 $mm^2$; and (xli) 3.90-4.00 $mm^2$.

The ion source preferably further comprises one or more heaters which are arranged and adapted to supply one or more heated streams of gas to the exit of the one or more nebulisers.

According to an embodiment:

(i) the one or more heaters surround the first capillary tube and are arranged and adapted to supply a heated stream of gas to the exit of the first capillary tube; and/or (ii) the one or more heaters comprise one or more infra-red heaters; and/or (iii) the one or more heaters comprise one or more combustion heaters.

The ion source may further comprise one or more heating devices arranged and adapted to directly and/or indirectly heat the one or more targets.

The one or more heating devices may comprise one or more lasers arranged and adapted to emit one or more laser beams which impinge upon the one or more targets in order to heat the one or more targets.

According to an embodiment the one or more targets are maintained, in use, at a potential: (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV.

According to an embodiment the one or more targets are maintained, in use, at a potential (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV; relative to the potential of an enclosure surrounding the ion source and/or an ion inlet device which leads to a first vacuum stage of a mass spectrometer and/or the one or more nebulisers.

According to a preferred embodiment in a mode of operation the one or more targets are maintained at a positive potential and the droplets impacting upon the one or more targets form a plurality of positively charged ions.

According to another preferred embodiment in a mode of operation the one or more targets are maintained at a negative potential and the droplets impacting upon the one or more targets form a plurality of negatively charged ions.

The ion source may further comprise a device arranged and adapted to apply a sinusoidal or non-sinusoidal AC or RF voltage to the one or more targets.

The one or more targets are preferably arranged or otherwise positioned so as to deflect the stream of droplets and/or the plurality of ions towards an ion inlet device of a mass spectrometer.

The one or more targets are preferably positioned upstream of an ion inlet device of a mass spectrometer so that ions are deflected towards the direction of the ion inlet device.

The one or more targets may comprise a stainless steel target, a metal, gold, a non-metallic substance, a semiconductor, a metal or other substance with a carbide coating, an insulator or a ceramic.

The one or more targets may comprise a plurality of target elements so that droplets from the one or more nebulisers cascade upon a plurality of target elements and/or wherein the target is arranged to have multiple impact points so that droplets are ionised by multiple glancing deflections.

The one or more targets may be shaped or have an aerodynamic profile so that gas flowing past the one or more targets is directed or deflected towards, parallel to, orthogonal to or away from an ion inlet device of a mass spectrometer.

At least some or a majority of the plurality of ions may be arranged so as to become entrained, in use, in the gas flowing past the one or more targets.

According to an embodiment in a mode of operation droplets from one or more reference or calibrant nebulisers are directed onto the one or more targets.

According to an embodiment in a mode of operation droplets from one or more analyte nebulisers are directed onto the one or more targets.

According to another aspect of the present invention there is provided a mass spectrometer comprising an ion source as described above.

The mass spectrometer preferably further comprises an ion inlet device which leads to a first vacuum stage of the mass spectrometer.

The ion inlet device preferably comprises an ion orifice, an ion inlet cone, an ion inlet capillary, an ion inlet heated capillary, an ion tunnel, an ion mobility spectrometer or separator, a differential ion mobility spectrometer, a Field Asymmetric Ion Mobility Spectrometer ("FAIMS") device or other ion inlet.

The one or more targets are preferably located at a first distance $X_1$ in a first direction from the ion inlet device and at a second distance $Z_1$ in a second direction from the ion inlet device, wherein the second direction is orthogonal to the first direction and wherein:

(i) $X_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm; and/or (ii) $Z_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

The one or more targets are preferably positioned so as to deflect the stream of droplets and/or the plurality of ions towards the ion inlet device.

The one or more targets are preferably positioned upstream of the ion inlet device.

The one or more targets preferably comprise either: (i) one or more rods; or (ii) one or more pins having a taper cone.

The stream of droplets is preferably arranged to impact the one or more rods or the taper cone of the one or more pins either: (i) directly on the centerline of the one or more rods or pins; or (ii) on the side of the one or more rods or the taper cone of the one or more pins which faces towards or away from the ion inlet orifice.

The mass spectrometer may further comprise an enclosure enclosing the one or more nebulisers, the one or more targets and the ion inlet device.

The mass spectrometer may further comprise one or more deflection or pusher electrodes, wherein in use one or more DC voltages or DC voltage pulses are applied to the one or more deflection or pusher electrodes in order to deflect or urge ions towards an ion inlet device of the mass spectrometer.

According to an aspect of the present invention there is provided a method of ionising a sample comprising:

causing a stream predominantly of droplets to impact upon one or more targets to ionise the droplets to form a plurality of analyte ions.

According to an aspect of the present invention there is provided a method of mass spectrometry comprising a method of ionising ions as described above.

According to an aspect of the present invention there is provided a mass spectrometer comprising:

an ion source including:

a target; and a nebuliser configured to emit, in use, a stream formed predominantly of droplets which are caused to impact upon the target and to ionise the droplets to form a plurality of ions.

According to an aspect of the present invention there is provided an ion source comprising:

a target; and a nebuliser configured to emit, in use, a stream formed predominantly of droplets which are caused to impact upon the target and to ionise the droplets to form a plurality of ions.

According to an aspect of the present invention there is provided a method of mass spectrometry comprising:

ionising a sample by generating a stream predominantly formed of droplets and ionising the droplets to form a plurality of ions by impacting the droplets upon one or more targets.

According to an aspect of the present invention there is provided a method of ionising a sample comprising generating a stream predominantly formed of droplets and ionising the droplets to form a plurality of ions by impacting the droplets upon one or more targets.

According to an aspect of the present invention there is provided a desolvation device comprising:

one or more nebulisers and one or more targets;

wherein one or more nebulisers are arranged and adapted to emit, in use, a stream predominantly of droplets which are caused to impact upon said one or more targets and to cause said droplets to form desolvated gas phase molecules and/or secondary droplets.

According to an aspect of the present invention there is provided a method of desolvation comprising:

causing a stream predominantly of droplets to impact upon one or more targets and to cause said droplets to form desolvated gas phase molecules and/or secondary droplets.

It will be apparent that the present invention extends beyond an ion source or method of ionising a sample to include apparatus and methods for at least partially desolvating or further desolvating a stream of droplets. The resulting gas phase molecules and/or secondary droplets may be subsequently ionised by a separate ion source.

According to an aspect of the present invention there is provided a mass spectrometer comprising:

a nebuliser comprising a first capillary tube and having an exit which emits, in use, a stream of analyte droplets; and a target arranged <10 mm from the exit of the nebuliser;

characterised in that the mass spectrometer further comprises:

a liquid chromatography separation device arranged and adapted to emit an eluent over a period of time; and an ion source arranged and adapted to ionise the eluent, the ion source comprising the nebuliser and wherein, in use, the stream of analyte droplets is caused to impact upon the target and to ionise the analyte to form a plurality of analyte ions.

By way of contrast, the target of a SACI ion source is placed downstream of the ion inlet orifice of a mass spectrometer and ions are reflected back towards the ion inlet orifice.

According to another aspect of the present invention there is provided a method of mass spectrometry comprising:

providing a nebuliser comprising a first capillary tube and having an exit which emits a stream of analyte droplets; and positioning a target <10 mm from the exit of the nebuliser;

characterised in that the method further comprises:

providing a liquid chromatography separation device which emits an eluent over a period of time; and ionising the eluent by causing the stream of analyte droplets to impact upon the target and to ionise the analyte to form a plurality of analyte ions.

As discussed above, the spray point of a SACI ion source is within the heated nebuliser probe so that the typical distance between the spray point and a target plate is around 70 mm. By way of contrast, with the preferred impactor ion source the spray point is located at the tip of the inner capillary tube and the distance between the spray point and the target may be <10 mm.

It will be understood by those skilled in the art that a SACI ion source emits a vapour stream and the impact velocity of the vapour upon the target is relatively low and is approximately 4 m/s. By way of contrast, the impactor ion source according to the preferred embodiment does not emit a vapour stream but instead emits a high density droplet stream. Furthermore, the impact velocity of the droplet stream upon the target is relatively high and is approximately 100 m/s.

It will be apparent therefore that the ion source according to the present invention is quite distinct from known SACI ion sources.

According to a preferred embodiment a liquid stream is preferably converted into a nebulised spray via a concentric flow of high velocity gas without the aid of a high potential difference at the sprayer or nebuliser tip. A micro target with comparable dimensions or impact zone to the droplet stream is preferably positioned in close proximity (e.g. <5 mm) to the sprayer tip to define an impact zone and to partially deflect the spray towards the ion inlet orifice of the mass spectrometer. The resulting ions and charged droplets are sampled by the first vacuum stage of the mass spectrometer.

According to the preferred embodiment the target preferably comprises a stainless steel target. However, other embodiments are contemplated wherein the target may comprise other metallic substances (e.g. gold) and non-metallic substances. Embodiments are contemplated, for example, wherein the target comprises a semiconductor, a metal or other substance with a carbide coating, an insulator or a ceramic.

According to another embodiment the target may comprise a plurality of plates or target elements so that droplets from the nebuliser cascade upon a plurality of target plates or target elements. According to this embodiment there are preferably multiple impact points and droplets are ionised by multiple glancing deflections.

From an API source perspective, the combination of a close-coupled impactor which also serves as a charged ionization surface provides the basis of a sensitive multimode ionization source. The spray tip and micro target are preferably configured in close proximity with a glancing impact geometry which results in increased spray flux at the target and significantly less beam divergence or reflected dispersion when compared to a known broad area SACI ion source. The preferred embodiment therefore provides a high sensitivity API source.

The preferred embodiment comprises a multimode ion source which advantageously can ionize high and low polarity analytes at high efficiency without the need to switch hardware or tuning parameters.

The droplets which impact the one or more targets are preferably uncharged.

It will be apparent that the ion source and method of ionising ions according to the present invention is particularly advantageous compared with a known SACI ion source.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
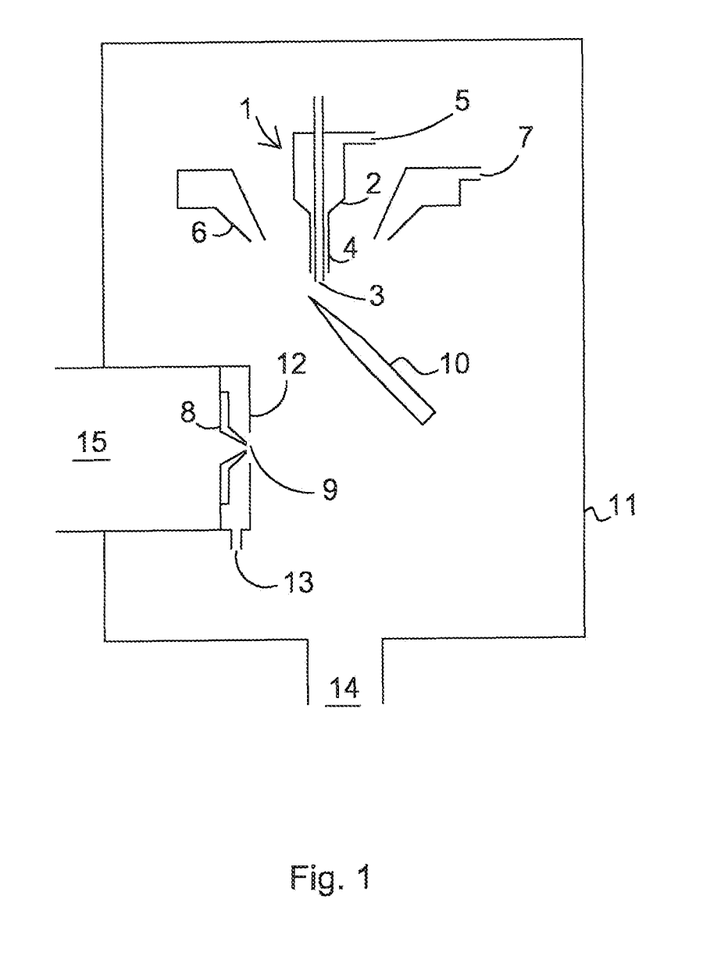
FIG. 1 shows an impactor spray API ion source according to a preferred embodiment of the present invention.

FIG. 1 shows a schematic of the general layout of an impactor spray API ion source according to an embodiment of the present invention. A flow of liquid containing analyte is arranged to enter a nebuliser or sprayer 1 and is delivered to the sprayer tip 2 via a liquid capillary tube 3. The liquid capillary tube 3 is preferably surrounded by a second capillary 4 which preferably includes a gas inlet 5 to deliver a stream of high velocity gas to the exit of the liquid capillary tube 3. According to an embodiment the inner diameter of the liquid capillary tube 3 is 130 μm and the outer diameter of the liquid capillary tube 3 is 270 μm. The inner diameter of the second (gas) capillary tube 4 is preferably 330 μm. This arrangement produces a nebulised spray which contains droplets with a typical diameter of 10-20 μm and which have velocities greater than 100 m/s at a close distance from the sprayer tip.

The resulting droplets are preferably heated by an additional flow of gas that enters a concentric heater 6 via a second gas inlet 7. The nebuliser or sprayer 1 may be hinged to the right hand side of the ion inlet cone 8 of a mass spectrometer so that it can swing to vary the horizontal distance between the sprayer tip and an ion inlet orifice 9. The probe may also configured such that the vertical distance between the sprayer tip and the ion inlet orifice 9 can also be varied. A target 10 which preferably has a similar dimension to that of the liquid capillary tube 3 is placed between the sprayer tip and the ion inlet orifice 9. The target 10 can preferably be manipulated in the x and y directions (in the horizontal plane) via a micro adjuster stage and is preferably held at a potential of 0-5 kV relative to a source enclosure 11 and the ion inlet orifice 9. The ion inlet cone 8 is surrounded by a metal cone gas housing 12 that is preferably flushed with a low flow of nitrogen gas that enters via a gas inlet 13. All gasses that enter the source enclosure preferably leave via a source enclosure exhaust 14 or the ion inlet orifice 9 which is pumped by the first vacuum stage 15 of the mass spectrometer.

Figure 2A:
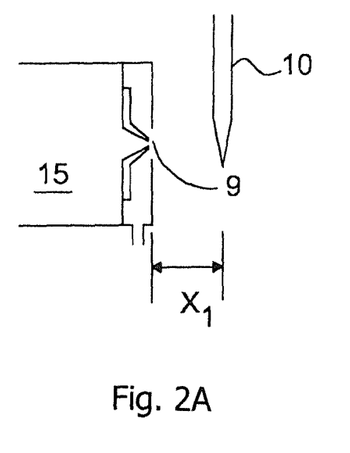
FIG. 2A shows a plan view of a target and a first vacuum stage of a mass spectrometer according to a preferred embodiment of the present invention with the nebuliser omitted and FIG. 2B shows a side view of the nebuliser or sprayer tip, target and first vacuum stage of a mass spectrometer according to a preferred embodiment of the present invention.
Figure 2B:
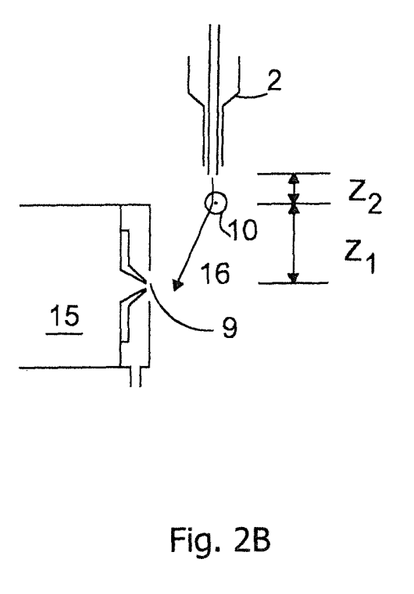

FIG. 2A shows a schematic plan view of an embodiment of the present invention with the nebuliser or sprayer 1 omitted. A target 10 is located adjacent the first vacuum stage 15 of the mass spectrometer. According to an embodiment the target 10 may comprise a 0.8 mm diameter stainless steel pin which preferably incorporates a straight taper section over a distance of 5 mm. The pin is preferably positioned at a horizontal distance $X_1$ of 5 mm from the ion inlet orifice 9. The pin 10 is preferably positioned such that the point of impact between the probe axis and the target 10 is on the side of the taper cone that faces the ion inlet orifice 9 as shown in FIG. 2B. This position results in an optimized glancing angle of incidence shown as an arrowed line 16 in the end view schematic of FIG. 2B. FIG. 2B also shows the relative vertical positions of the nebuliser or probe 2 and target 10 according to the preferred embodiment i.e. $Z_1$=9 mm and $Z_2$=1.5 mm. The nebuliser or sprayer 2 is preferably maintained at 0V, the target 10 is preferably held at 2.2 kV, the ion inlet cone is preferably held at 100 V, the cone gas housing is preferably held at 100 V and the heater assembly and source enclosure are preferably held at ground potential. The nitrogen nebuliser gas is preferably pressurized to 7 bar, the nitrogen heater gas flow is preferably pressurized to deliver 1200 L/hr and the nitrogen cone gas flow is preferably pressurized to deliver 150 L/hr.

A series of tests were conducted to test the relative sensitivities of the preferred impactor spray source, a conventional ESI ion source and a conventional APCI ion source.

The conventional ESI ion source was constructed by removing the target 10 and applying a potential of 2.5 kV directly to the sprayer tip. All other potentials and gas flows were maintained as above.

Figure 3:
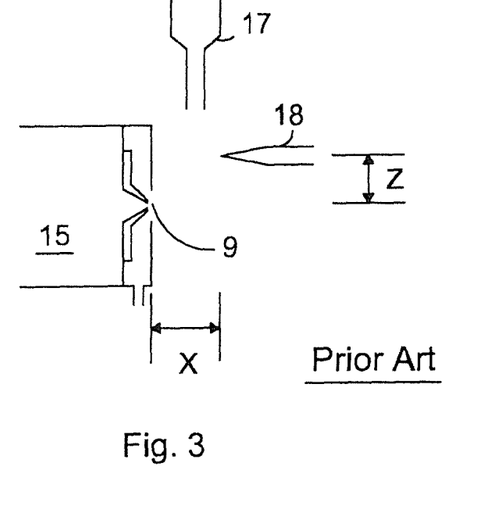
FIG. 3 shows a conventional APCI ion source with a corona discharge pin.

The APCI ion source was constructed by replacing the nebuliser or sprayer 2 with a conventional heated nebuliser probe 17 as shown in FIG. 3 as used in commercial APCI ion sources and adding a corona discharge pin 18. The tip of the corona discharge pin 18 was located at a distance X=7 mm and Z=5.5 mm as shown in FIG. 3. The APCI ion source probe was operated at 550° C., the heater gas was unheated at a flow rate of 500 L/hr and the corona discharge pin 18 was set at a current of 5 μA. All other settings were as described above.

A test solution was prepared consisting of 70/30 acetonitrile/water and containing sulphadimethoxine (10 pg/μL), verapamil (10 pg/μL), erythromycin (10 pg/μL), cholesterol (10 ng/µL) and cyclosporin (100 pg/µL). The test solution was infused at a flow rate of 15 µL/min into a carrier liquid flow of 0.6 mL/min of 70/30 acetonitrile/water which was then sampled by the three different API ion sources.

Figure 4:
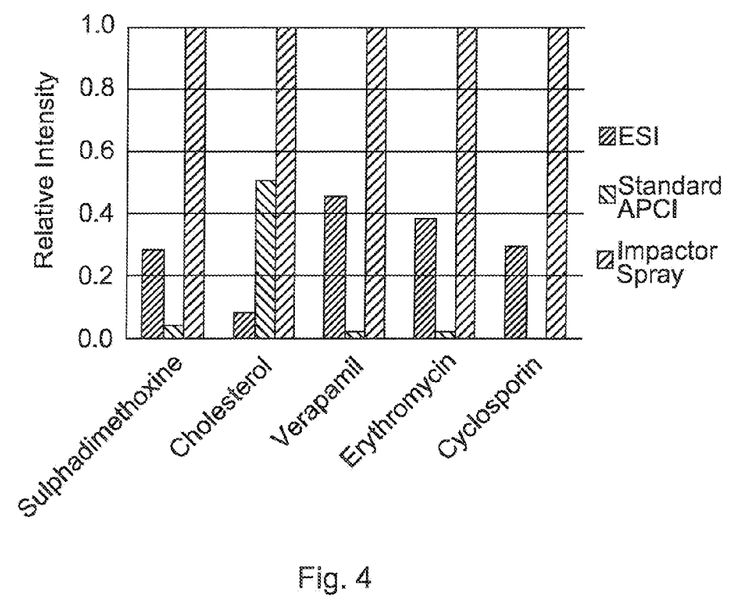
FIG. 4 shows the relative intensities of five test analytes measured using a conventional Electrospray ion source, a conventional APCI ion source and an impactor ion source according to the preferred embodiment.

FIG. 4 shows the relative signal intensities obtained for the five test analytes with a conventional Electrospray ion source, a conventional APCI ion source and an impactor ion source according to the preferred embodiment. For each analyte the signal intensity was monitored for the protonated molecule ([M+H]$^+$). However, owing to signal saturation with the preferred impactor spray, the cholesterol signal was measured on the carbon-13 isotope of the [M+H]$^+$ ion. From this figure, it is clear that although the APCI ion source has some advantages over ESI ion sources (e.g. for non-polar analytes such as cholesterol), ESI is generally the more sensitive of these two techniques. It is also clear that the preferred impactor spray source gives rise to significantly greater signal intensities than either the ESI or APCI ion source for all compound types.

Figure 5:
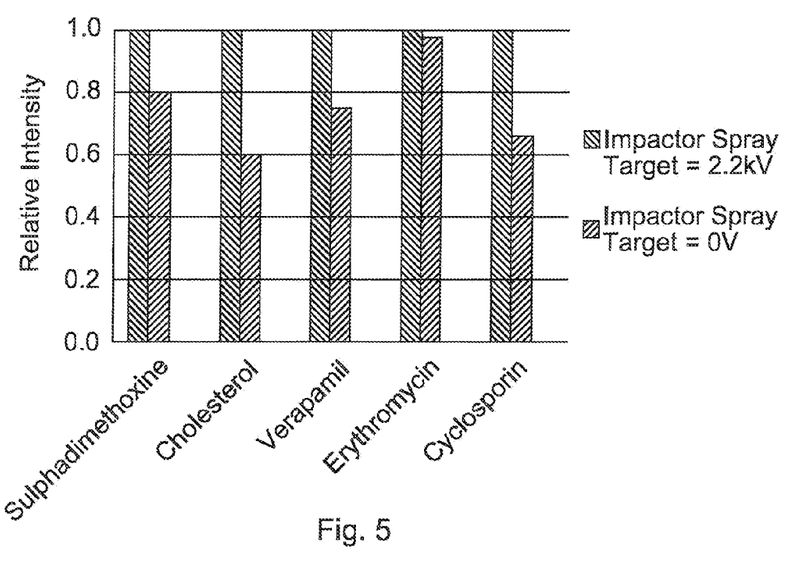
FIG. 5 shows the effect of target potential on ion signal according to a preferred embodiment of the present invention.

In API ion sources that utilize the SACI ionization technique, a broad area target is maintained at an elevated potential to optimize ion signal. FIG. 5 shows the effect of varying the target potential on the resulting ion signal for the preferred impactor spray source where the same test mixture was analysed with a target potential of 2.2 kV followed by a target potential of 0 kV. In contrast to SACI, it is apparent that an elevated target potential, although advantageous, is not essential to the ionization process. By contrast, a broad area SACI source would lose >90% of the ion signal under the same experimental conditions (data not shown).

Figure 6A:
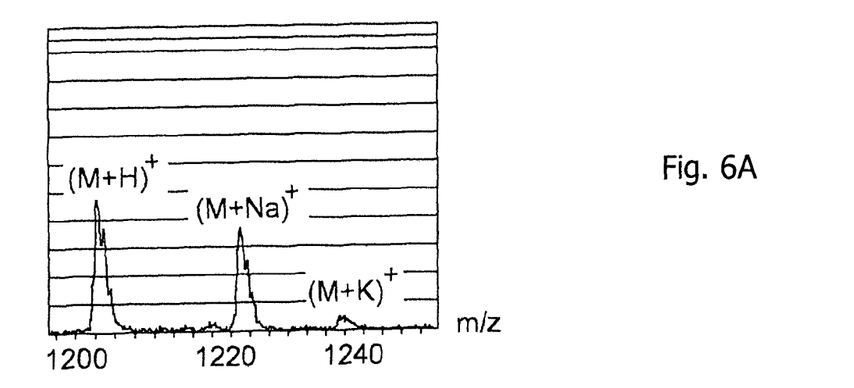
FIG. 6A shows a mass spectrum obtained from an impactor spray ion source according to a preferred embodiment of the present invention with a target potential of 2.2 kV.
Figure 6B:
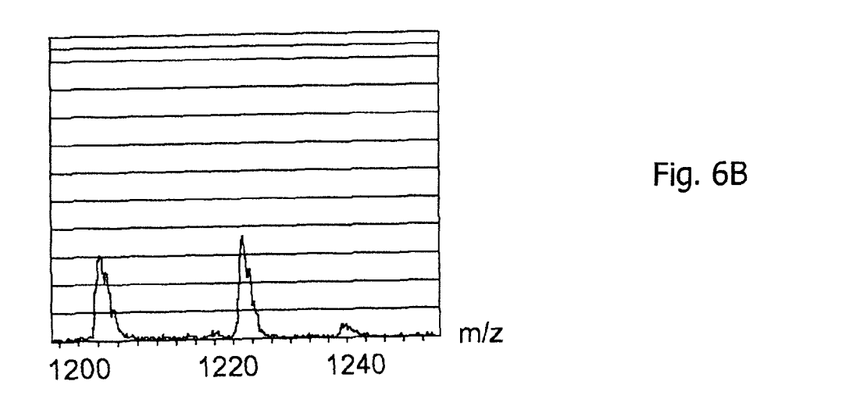
FIG. 6B shows a mass spectrum obtained from an impactor spray source according to an embodiment of the present invention with a target potential of 0V and FIG. 6C shows a mass spectrum obtained with a conventional Electrospray ion source with an optimized capillary potential of 4 kV.
Figure 6C:
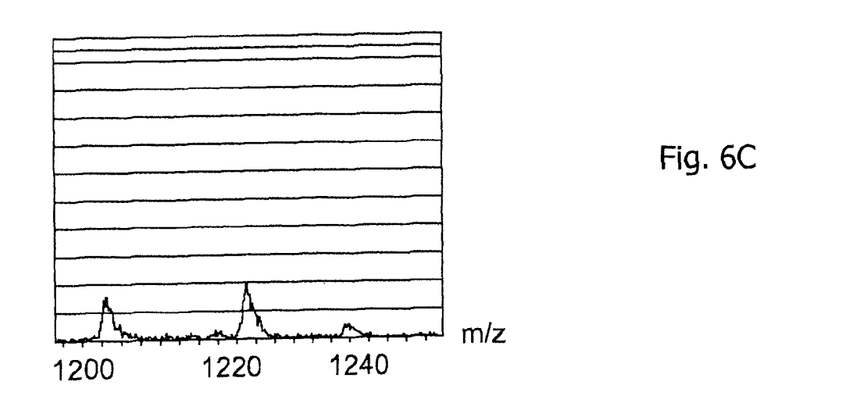

Although not essential, an elevated target potential is nonetheless advantageous and has the result of improving the qualitative aspects of mass spectral data. To illustrate this, FIG. 6A shows a mass spectrum obtained from an impactor ion source according to the preferred embodiment with a target potential of 2.2 kV, FIG. 6B shows a mass spectrum obtained from an impactor ion source according to an embodiment with a target potential of 0 V and FIG. 6C shows a mass spectrum obtained with a conventional electrospray source with an optimized capillary potential of 4 kV. The mass spectra shown in FIGS. 6A and 6B which were obtained using an ion source according to the preferred embodiment are shown to produce more analyte ions than ESI but significantly an elevated target potential also reduces the susceptibility to ion adduct formation ([M+Na]$^+$ and [M+K]$^+$) such that the protonated molecule ([M+H]$^+$) is the base peak only for the mass spectrum shown in FIG. 6A.

Figure 7:
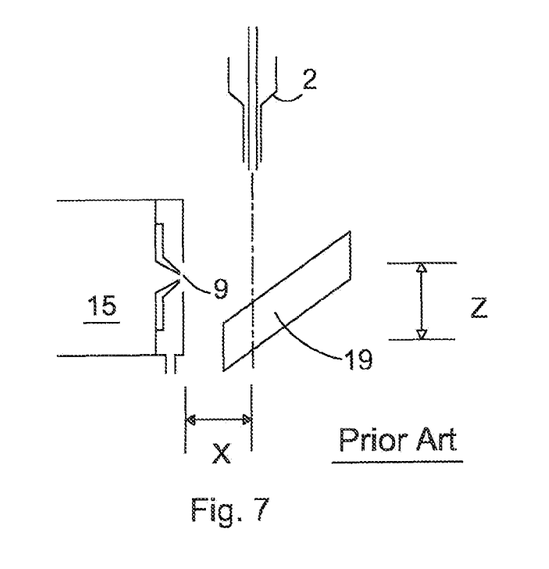
FIG. 7 shows a known Surface Activated Chemical Ionisation ion source.

An experiment was conducted to compare the sensitivity of the impactor ion source according to the preferred embodiment with a SACI-type ionization source. FIG. 7 shows a schematic of the SACI ion source which was used. The SACI ion source was constructed by replacing the impactor pin target 10 with a 0.15 mm thick rectangular tin sheet 19 which measured approximately 30 mm×15 mm. The sheet target 19 was angled at approximately 30° to horizontal and was positioned such that the point of intersection between the nebuliser or probe 2 axis and the target 19 was at X=4 mm and Z=4 mm. The SACI ion source was optimised at a nebuliser or sprayer potential of 0 V and a target potential of 1 kV. All other gas flows and voltages were as described for the preferred impactor spray source.

Figure 8:
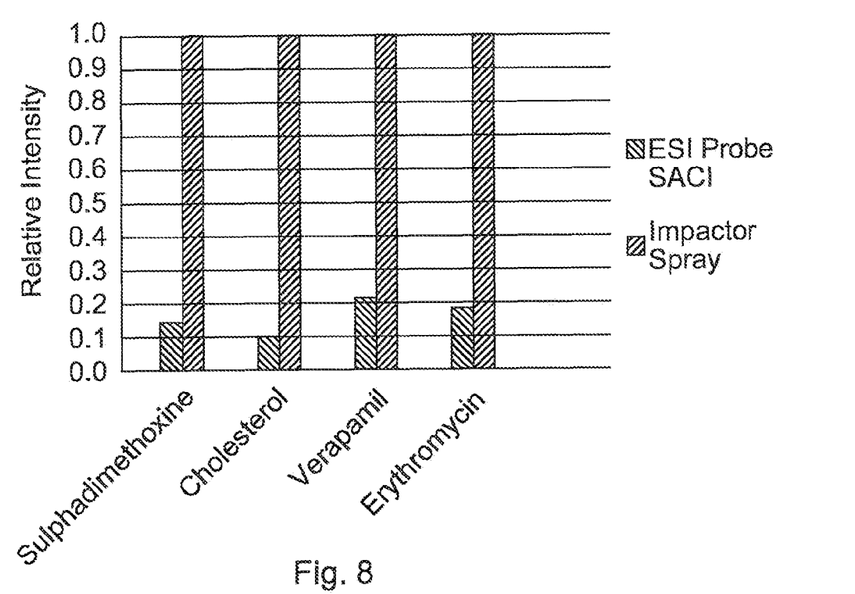
FIG. 8 shows a comparison of the relative intensities obtained with a conventional SACI ion source and an impactor ion source spray according to a preferred embodiment.

FIG. 8 compares the relative signal intensities obtained with a SACI ion source and an impactor ion source according to the preferred embodiment. It is observed that the preferred impactor spray ion source is typically between x5-10 more sensitive than the broad area SACI ion source.

Further embodiments are contemplated wherein the performance of the preferred impactor ion source may be further improved by positioning a central wire in the bore of the liquid capillary tube 3. Video photography has shown that the central wire focuses the droplet stream such that the target may be placed at the focal point to further increase the droplet flux density. The position of the focal point is comparable to the sprayer tip/target distance used in the preferred embodiment (1-2 mm).

As described above a SACI ion source converts a liquid stream into a vapour stream that then impinges on a broad area target. Experiments on SACI (Cristoni et al., J. Mass Spectrom., 2005, 40, 1550) have shown that ionisation occurs as a result of the interaction of neutral analyte molecules in the gas phase with the proton rich surface of the broad area target. Furthermore, there is a linear relationship between ionisation efficiency and target area within the range 1-4 cm$^2$.

In contrast to SACI, the preferred ion source uses a streamlined target to intercept a high velocity stream of liquid droplets which results in a secondary stream consisting of secondary droplets, gas phase neutrals and ions.

A pneumatic nebuliser according to an embodiment of the present invention was investigated further. The nebuliser comprised an inner liquid capillary with an internal diameter of 127 µm and an outer diameter of 230 µm. The inner liquid capillary was surrounded by a gas capillary with an internal diameter of 330 µm that was pressurised to 7 bar.

Figure 9:
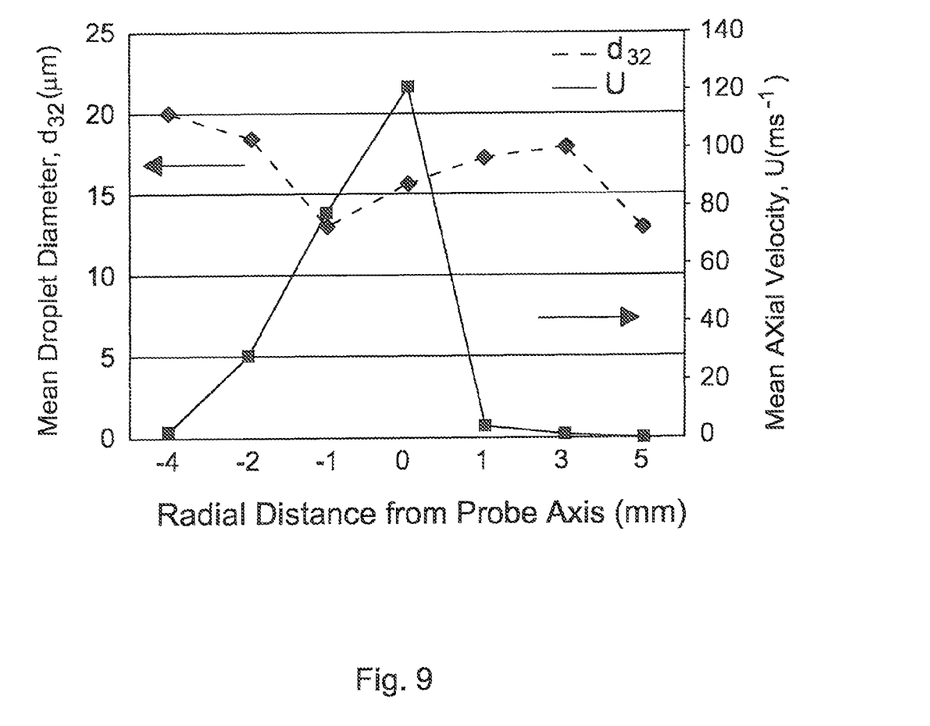
FIG. 9 shows data obtained from a Phase Doppler Anemometry analysis of the droplets emitted from a preferred nebuliser.

FIG. 9 shows typical data obtained from a Phase Doppler Anemometry ("PDA") analysis of the preferred nebuliser for a 1 mL/min liquid flow consisting of 90% water/10% methanol and a nitrogen nebuliser gas.

The PDA sampling point was scanned radially across the spray (probe axis=0) at an axial distance of 5 mm from the spray point i.e. equivalent to the typical nebuliser/target distance according to the preferred embodiment. FIG. 9 shows that the nebuliser typically produces liquid droplets with a Sauter mean diameter ($d_{32}$) in the range 13-20 µm with mean axial velocities in excess of 100 ms$^{-1}$.

FIG. 9 also shows that the very high velocity droplets are well collimated and are typically confined within a radius of 1 mm from the probe axis.

Figure 10:
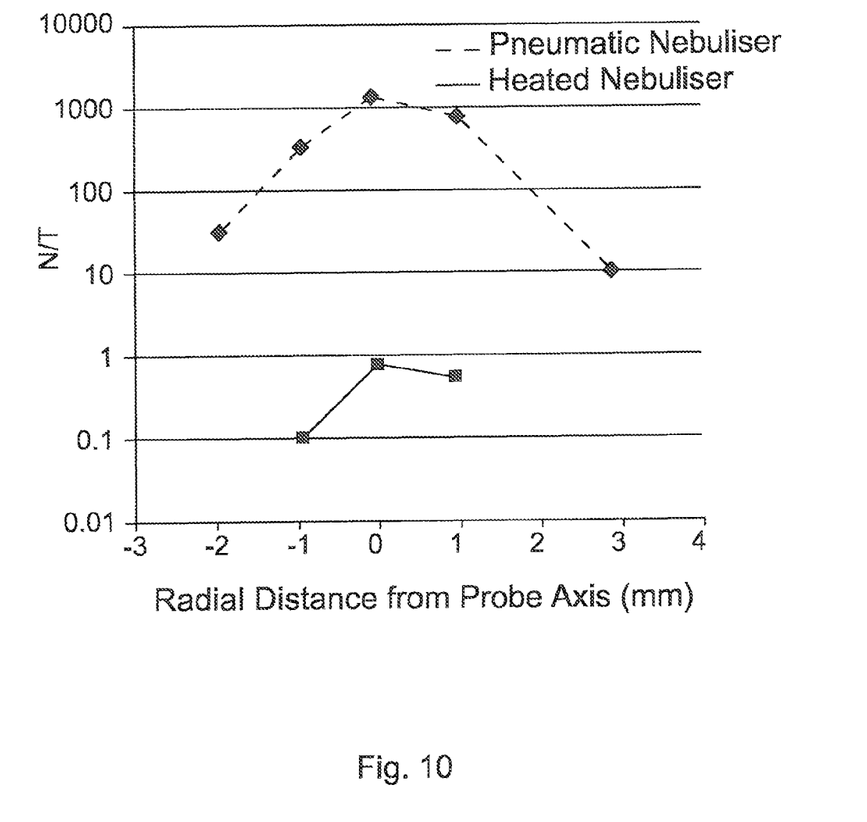
FIG. 10 shows a comparison of the radial distribution of the data rate for a pneumatic nebuliser according to an embodiment of the present invention and from a heated nebuliser such as used in a SACI ion source.

The upper trace of FIG. 10 shows the radial distribution of the data rate N/T (number of validated samples per unit time) for the preferred pneumatic nebuliser and experimental conditions as described above. This logrithmic plot demonstrates that the spray is well collimated with greater than two thirds of the total droplet mass being confined to a radius of 1 mm from the probe axis. The lower trace of FIG. 10 shows the equivalent N/T distribution from a heated nebuliser such as used in a conventional SACI source. The heated nebuliser consists of a pneumatic nebuliser which sprays into a 90 mm long cylindrical tube with a 4 mm diameter bore (tube temperature=600° C.). The N/T data for this nebuliser was obtained at an axial distance of 7 mm from the exit end of the heated tube. It is important to note that the N/Ts for the few detected droplets from the heated nebuliser (d32 was typically 14 µm, data not shown) are typically three orders of magnitude lower than those obtained from the pneumatic nebuliser according to the preferred embodiment. This is a due to the fact that the overwhelming mass of the liquid is vaporised in the SACI-type heated nebuliser resulting in a stream of vapour that contains a very low number density of surviving droplets.

Accordingly, a known SACI ion source should be construed as comprising a nebuliser which emits a stream predominantly of vapour and hence a SACI ion source should be understood as not falling within the scope of the present invention.

Referring to the data presented in FIGS. 9 and 10 it can be assumed that the physical model of the ion source according to the preferred embodiment is dominated by the impact of high velocity liquid droplets on a target that is indirectly heated by the source heater. Such impact effects give rise to the formation of secondary droplets, where the nature of the droplet breakup is determined by the Weber number $W_e$ which is given by the following:

$$W_e = \rho U^2 d/\sigma \quad (1)$$

wherein $\rho$ is the droplet density, U is the droplet velocity, d is the droplet diameter and $\sigma$ is the droplet surface tension.

If it is assumed that the water droplets are at 40° C., the nitrogen gas environment is at 100° C., d=18 µm and U=50 ms$^{-1}$ then a value of $W_e$=640 is obtained for the droplets according to the preferred embodiment. It has been shown (in the literature) that the number of reatomised water droplets increases linearly with $W_e$ in the range 50-750 for impact on a heated steel target for temperatures between 260-400° C. At $W_e$=750, a single droplet typically gave rise to 40 secondary droplets.

It is apparent, therefore, that the impactor target leads to significant droplet breakup to produce a secondary stream that consists of charged droplets, neutrals, ions and clusters.

The impact efficiency of the system will be largely governed by the Stokes number $S_k$ where:

$$S_k = \rho d^2 U / 18\mu a \quad (2)$$

wherein $\rho$ is the droplet density, d is the droplet diameter, U is the droplet velocity, $\mu$ is the gas viscosity and a is the characteristic dimension of the target.

Impact efficiency increases with increasing $S_k$ and thus favours large droplets with high velocity and a small target diameter. Thus for the preferred impactor spray conditions described above, it may be expected that $S_k$ has a typical value of 30.

For $S_k$>>1 droplets are highly likely to deviate from the flow streamlines and impact upon the target. In contrast, if the target dimension is increased by an order of magnitude and the velocity is decreased by an order of magnitude (i.e. similar conditions to SACI), then the value of $S_k$ drops to 0.3 at which point the droplets are more likely to follow the gas flow around the target. The impact efficiency is also known to increase with reducing Reynolds numbers which will further favour the streamlined nature of the impactor spray target according to the preferred embodiment.

The shape of the secondary stream will be governed by the gas flow dynamics and, in particular, the Reynolds number ($R_e$) which is given by:

$$R_e = \rho v L/\mu \quad (3)$$

wherein ρ is the gas density, v is the gas velocity, μ is the gas viscosity and L is the significant dimension of the target.

With a 1 mm diameter impactor target, a gas velocity of 50 $ms^{-1}$ and nitrogen gas at 100° C. then a value of $R_e$=3000 is obtained.

Reynolds numbers in the range 2000-3000 generally correspond to the transition region from laminar to turbulent flow. Therefore, it can be expected that the wake from the target contains some turbulence and eddy features, However, severe turbulence that could hinder the sampling of ions or droplets at the ion inlet cone is not expected.

The preferred ion source can be tuned by swinging the nebuliser to move the impact zone from one side of the rod-like target to the other. This results in changes to the wake which can be visually observed by strong illumination of the secondary droplet stream. Other embodiments are therefore also contemplated wherein similar source optimisation could be achieved with a centralised impact zone and a non-symmetric target cross section e.g. (the profile of) an aircraft wing.

Although the present invention has been described with reference to preferred embodiments it will be apparent to those skilled in the art that various changes in form and detail may be made without departing from the scope of the invention as defined by the accompanying claims.

The invention claimed is:

1. An ion source comprising:

one or more nebulisers and one or more targets;

wherein said one or more nebulisers are arranged and adapted to nebulise one or more eluents emitted by one or more liquid chromatography separation devices over a period of time;

wherein said one or more eluents have a liquid flow rate selected from the group consisting of: (i) 1-10 μL/min; (ii) 10-50 μL/min; (iii) 50-100 μL/min; (iv) 100-200 μL/min; (v) 200-300 μL/min; (vi) 300-400 μL/min; (vii) 400-500 μL/min; (viii) 500-600 μL/min; (ix) 600-700 μL/min; (x) 700-800 μL/min; (xi) 800-900 μL/min; (xii) 900-1000 μL/min; (xiii) 1000-1500 μL/min; (xiv) 1500-2000 μL/min; (xv) 2000-2500 μL/min; and (xvi) >2500 μL/min;

wherein said one or more nebulisers are arranged and adapted to emit, in use, a stream predominantly of droplets which are caused to impact upon said one or more targets and to ionise said droplets to form a plurality of ions;

wherein a mean axial impact velocity of said droplets upon said one or more targets is ≥20 m/s.

2. An ion source as claimed in claim 1, wherein said droplets comprise analyte droplets and said plurality of ions comprise analyte ions.

3. An ion source as claimed in claim 1, wherein said droplets comprise reagent droplets and said plurality of ions comprise reagent ions.

4. An ion source as claimed in claim 3, further comprising one or more tubes arranged and adapted to supply one or more analyte or other gases to a region adjacent said one or more targets.

5. An ion source as claimed in claim 4, wherein said reagent ions are arranged so as to ionise said analyte gas to form a plurality of analyte ions.

6. An ion source as claimed in claim 3, wherein said one or more targets are coated with one or more liquid, solid or gelatinous analytes and wherein said one or more analytes are ionised to form a plurality of analyte ions.

7. An ion source as claimed in claim 3, wherein said one or more targets are formed from one or more analytes and wherein said one or more analytes are ionised to form a plurality of analyte ions.

8. An ion source as claimed in claim 1, wherein an analyte liquid is supplied to said one or more targets and is ionised to form a plurality of analyte ions or a reagent liquid is supplied to said one or more targets and is ionised to form reagent ions which transfer charge to neutral analyte atoms or molecules to form analyte ions or which enhance the formation of analyte ions.

9. An ion source as claimed in claim 1, wherein said one or more nebulisers are arranged and adapted such that a majority of mass or matter emitted by said one or more nebulisers is formed of droplets not vapour.

10. An ion source as claimed in claim 1, wherein said one or more nebulisers are arranged and adapted to emit a stream of droplets wherein a Sauter mean diameter ("SMD", d32) of said droplets is in a range: (i) <5 µm; (ii) 5-10 µm; (iii) 10-15 µm; (iv) 15-20 µm; (v) 20-25 µm; or (vi) >25 µm.

11. An ion source as claimed in claim 1, wherein said stream of droplets emitted from said one or more nebulisers forms a stream of secondary droplets after impacting said one or more targets.

12. An ion source as claimed in claim 1, wherein said one or more nebulisers comprises a first capillary tube having an exit which emits, in use, said stream of droplets.

13. An ion source as claimed in claim 1, further comprising one or more heaters which are arranged and adapted to supply one or more heated streams of gas to an exit of said one or more nebulisers.

14. An ion source as claimed in claim 1, further comprising one or more heating devices arranged and adapted to directly or indirectly heat said one or more targets.

15. An ion source as claimed in claim 1, wherein in a mode of operation said one or more targets are maintained at a positive potential and wherein said droplets impacting upon said one or more targets form a plurality of positively charged ions.

16. An ion source as claimed in claim 1, wherein in a mode of operation said one or more targets are maintained at a negative potential and wherein said droplets impacting upon said one or more targets form a plurality of negatively charged ions.

17. An ion source as claimed in claim 1, further comprising a device arranged and adapted to apply a sinusoidal or non-sinusoidal AC or RF voltage to said one or more targets.

18. An ion source as claimed in claim 1, wherein said one or more targets are arranged or otherwise positioned so as to deflect said stream of droplets or said plurality of ions towards an ion inlet device of a mass spectrometer.

19. An ion source as claimed in claim 1, wherein said one or more targets are positioned upstream of an ion inlet device of a mass spectrometer so that ions are deflected towards said ion inlet device.

20. An ion source as claimed in claim 1, wherein said one or more targets comprise a plurality of target elements so that droplets from said one or more nebulisers cascade upon a plurality of target elements or wherein said target is arranged to have multiple impact points so that droplets are ionised by multiple glancing deflections.

21. An ion source as claimed in claim 1, wherein said one or more targets are shaped so that gas flowing past said one or more targets is directed or deflected towards, parallel to, orthogonal to or away from an ion inlet device of a mass spectrometer.

22. A mass spectrometer comprising an ion source as claimed in claim 1.

23. A mass spectrometer as claimed in claim 22, further comprising an ion inlet device which leads to a first vacuum stage of said mass spectrometer.

24. A mass spectrometer as claimed in claim 23, wherein said ion inlet device comprises an ion orifice, an ion inlet cone, an ion inlet capillary, an ion inlet heated capillary, an ion tunnel, an ion mobility spectrometer or separator, a differential ion mobility spectrometer, a Field Asymmetric Ion Mobility Spectrometer ("FAIMS") device or other ion inlet.

25. A mass spectrometer as claimed in claim 24, wherein the one or more targets comprise either one or more rods or one or more pins having a taper cone, said stream of droplets is arranged to impact said one or more rods or said taper cone of said one or more pins either: (i) directly on a centerline of said one or more rods or pins; or (ii) on a side of said one or more rods or said taper cone of said one or more pins which faces towards or away from said ion orifice.

26. An ion source comprising:
one or more nebulisers and one or more targets;
wherein said one or more nebulisers are arranged and adapted to nebulise one or more eluents emitted by one or more liquid chromatography separation devices over a period of time;
wherein said one or more eluents have a liquid flow rate selected from the group consisting of: (i) 1-10 µL/min; (ii) 10-50 µL/min; (iii) 50-100 µL/min; (iv) 100-200 µL/min; (v) 200-300 µL/min; (vi) 300-400 µL/min; (vii) 400-500 µL/min; (viii) 500-600 µL/min; (ix) 600-700 µL/min; (x) 700-800 µL/min; (xi) 800-900 µL/min; (xii) 900-1000 µL/min; (xiii) 1000-1500 µL/min; (xiv) 1500-2000 µL/min; (xv) 2000-2500 µL/min; and (xvi) >2500 µL/min;
wherein said one or more nebulisers are arranged and adapted to emit, in use, a stream predominantly of droplets which are caused to impact upon said one or more targets and to ionise said droplets to form a plurality of ions; and
wherein said one or more targets are arranged <10 mm from an exit of said one or more nebulisers.

27. A method of ionising a sample comprising:
nebulising one of more eluents emitted by one or more liquid chromatography separation devices over a period of time;
wherein said one or more eluents have a liquid flow rate selected from the group consisting of: (i) 1-10 µL/min; (ii) 10-50 µL/min; (iii) 50-100 µL/min; (iv) 100-200 µL/min; (v) 200-300 µL/min; (vi) 300-400 µL/min; (vii) 400-500 µL/min; (viii) 500-600 µL/min; (ix) 600-700 µL/min; (x) 700-800 µL/min; (xi) 800-900 µL/min; (xii) 900-1000 µL/min; (xiii) 1000-1500 µL/min; (xiv) 1500-2000 µL/min; (xv) 2000-2500 µL/min; and (xvi) >2500 µL/min;
causing a stream predominantly of droplets to impact upon one or more targets to ionise said droplets to form a plurality of analyte ions;
wherein a mean axial impact velocity of said droplets upon said one or more targets is ≥20 m/s.

28. A method of mass spectrometry comprising a method of ionising a sample as claimed in claim 27.

29. A method of ionising a sample comprising:
nebulising one of more eluents emitted by one or more liquid chromatography separation devices over a period of time;
wherein said one or more eluents have a liquid flow rate selected from the group consisting of: (i) 1-10 µL/min; (ii) 10-50 µL/min; (iii) 50-100 µL/min; (iv) 100-200 µL/min; (v) 200-300 µL/min; (vi) 300-400 µL/min; (vii) 400-500 µL/min; (viii) 500-600 µL/min; (ix) 600-700 µL/min; ($x$) 700-800 µL/min; (xi) 800-900 µL/min; (xii) 900-1000 µL/min; (xiii) 1000-1500 µL/min; (xiv) 1500-2000 µL/min; (xv) 2000-2500 µL/min; and (xvi) >2500 µL/min;
causing a stream predominantly of droplets to impact upon one or more targets to ionise said droplets to form a plurality of analyte ions;
wherein said stream is emitted by one or more nebulisers and wherein said one or more targets are arranged <10 mm from an exit of said one or more nebulisers.

* * * * *